(12) United States Patent
Woodward et al.

(10) Patent No.: US 9,068,694 B2
(45) Date of Patent: Jun. 30, 2015

(54) METHOD OF CONTROLLING BY-PRODUCTS OF VITAMIN C DEGRADATION AND IMPROVING PACKAGE INTEGRITY SHELF LIFE

(75) Inventors: D. Craig Woodward, Plano, TX (US); Justin L. Batson, Mansfield, TX (US)

(73) Assignee: PHILIP J. GORDON CONSULTANTS, INC., Richardson, TX (US)

( * ) Notice: Subject to any disclaimer, the term of this patent is extended or adjusted under 35 U.S.C. 154(b) by 909 days.

(21) Appl. No.: 13/136,884

(22) Filed: Aug. 12, 2011

(65) Prior Publication Data

US 2012/0067431 A1  Mar. 22, 2012

Related U.S. Application Data

(60) Provisional application No. 61/403,826, filed on Sep. 22, 2010, provisional application No. 61/459,740, filed on Dec. 17, 2010.

(51) Int. Cl.
| | |
|---|---|
| *A61K 8/67* | (2006.01) |
| *A61K 31/375* | (2006.01) |
| *B01L 3/02* | (2006.01) |
| *B65D 47/18* | (2006.01) |
| *B65D 41/04* | (2006.01) |
| *B65D 53/04* | (2006.01) |
| *B67B 6/00* | (2009.01) |
| *F17D 3/00* | (2006.01) |
| *B65D 1/08* | (2006.01) |

(52) U.S. Cl.
CPC .............. *F17D 3/00* (2013.01); *Y10T 137/0396* (2015.04); *B65D 53/04* (2013.01); *B65D 47/18* (2013.01); *B01L 3/0282* (2013.01); *A61K 31/375* (2013.01); *B65D 41/045* (2013.01); *B65D 1/08* (2013.01); *B01L 3/0272* (2013.01); *A61K 8/676* (2013.01); *B67B 6/00* (2013.01)

(58) Field of Classification Search
CPC ....... B01L 3/0282; B01L 3/0272; B67B 6/00; B65D 1/08; B65D 47/18; B65D 41/045; B65D 53/04; A61K 31/375; A61K 8/676
USPC .......... 53/410, 420, 421; 141/22–24; 222/420, 222/633; 514/474; 215/261; 422/934
See application file for complete search history.

(56) References Cited

U.S. PATENT DOCUMENTS

| | | | | |
|---|---|---|---|---|
| 1,313,566 | A | * | 8/1919 | Trowbridge .................... 141/24 |
| 2,707,469 | A | | 5/1955 | Feinstein |
| 3,158,183 | A | * | 11/1964 | Brown et al. .................... 141/24 |
| 3,406,875 | A | * | 10/1968 | Park ............................... 141/24 |

(Continued)

FOREIGN PATENT DOCUMENTS

| | | | | |
|---|---|---|---|---|
| GB | 814161 | A * | 5/1959 | ............ B01L 3/0282 |
| GB | 854163 | A * | 11/1960 | ............ B01L 3/0282 |

*Primary Examiner* — Stephen F Gerrity
(74) *Attorney, Agent, or Firm* — Maryellen Feehery Hank; Reed Smith LLP

(57) ABSTRACT

The invention is a method of venting the degradation products of an ascorbic acid containing composition. This prevents a build-up of carbon dioxide and may prolong the life of the packaging. The packaging includes an impermeable container and a semi-permeable top, which allows carbon dioxide to vent over time. When the composition includes water, the surface area of semi-permeable material contacting the composition is reduced to lessen water vapor loss.

18 Claims, 15 Drawing Sheets

(56) References Cited

U.S. PATENT DOCUMENTS

| | | | |
|---|---|---|---|
| 3,961,088 A * | 6/1976 | Besand et al. | 426/262 |
| 5,140,043 A | 8/1992 | Darr et al. | |
| 5,154,702 A * | 10/1992 | Foyil | 222/420 |
| 5,730,306 A * | 3/1998 | Costa et al. | 215/261 |
| 6,238,713 B1 * | 5/2001 | Von Rhein | 426/72 |
| H002044 H * | 9/2002 | Faughey et al. | 141/22 |
| 2003/0098321 A1 * | 5/2003 | Kaposi | 222/420 |
| 2009/0230078 A1 * | 9/2009 | Walsh | 215/261 |
| 2010/0065528 A1 | 3/2010 | Hanafusa et al. | |
| 2010/0233024 A1 * | 9/2010 | Whiting et al. | 422/41 |

\* cited by examiner

METHOD OF CONTROLLING BY-PRODUCTS OF VITAMIN C DEGRADATION AND IMPROVING PACKAGE INTEGRITY SHELF LIFE

BACKGROUND OF THE INVENTION

Numerous compositions, ranging from use in cosmetic to food to industrial and other applications, include ascorbic acid. The problem is that ascorbic acid is unstable, especially in solution, and carbon dioxide (among other things) is generated when ascorbic acid degrades. This degradation process occurs faster when the composition is exposed to higher temperature and can cause the compositions to spoil or change color or otherwise be unfit for consumption or use. Additionally, packaging for the composition often fails due to the pressure generated by the degradation process. This is a costly problem for many industries and is a particular issue for compositions which contain at least about 0.1% by weight ascorbic acid. It is to be understood that all percentages given in this specification are by weight unless otherwise noted.

In the prior art, there are several methods used to slow the degradation of ascorbic acid. Each of the following and any combination thereof have been used: reducing the availability of oxygen, reducing the pH of the composition, adding oxygen scavengers, labeling the compositions with accelerated expiration dates, and storing in controlled climates such as under refrigeration. While these methods work up to a point, none have been sufficient in preventing ascorbic acid degradation.

The degradation of ascorbic acid, especially in solution, is inevitable. Color change is a concern because an ascorbic acid composition will darken over time, at times even before the consumer purchases the composition. A greater concern is the generation of carbon dioxide, which this invention addresses. Carbon dioxide is a direct result of the degradation of ascorbic acid. Since the degradation is accelerated at elevated temperatures, shipping under uncontrolled temperatures may lead to accelerated carbon dioxide generation. Packaging the compositions in air tight containers helps prevent oxygen from degrading the ascorbic acid; however, this packaging can cause an undesirable buildup of carbon dioxide. This buildup may cause premature package failure, or create a pressurized composition, which foams upon opening, resulting in loss of composition.

Furthermore, if a composition is shipped over long distances, such as overseas, the degradation problem is often exacerbated because of the inability to control temperatures during transit. The length of transit time also reduces the shelf life for the composition after transit and causes further degradation of the composition resulting in the excess production of carbon dioxide.

Many of the compositions, which include ascorbic acid, are packaged in glass, vial type containers with a bulb, usually comprised of rubber, and a bulb cap (unlike a service cap, the bulb cap has a hole in the center in which the bulb is located) or a service cap with no bulb. This package type is intended to be an airtight environment, which is considered to be ideal for packaging ascorbic acid-containing compositions. Rubber and other impermeable materials are commonly used in this packaging because they prevent oxygen from contacting the composition. As ascorbic acid breaks down, one of the by-products of the reaction is carbon dioxide. Carbon dioxide gas can build up in these bulbs, causing bulb expansion and package failure. The rate of production of carbon dioxide is rapid and creates problems with maintaining the package's integrity. The consumer sees the bulb expand with carbon dioxide and finds it cosmetically unappealing and evidence that the product has surpassed its shelf life and is no longer acceptable for use.

In some compositions, the carbon dioxide will dissolve back into the composition and create a "carbonated effect" that foams excessively on opening. This is especially true when a service cap is used in place of the rubber bulb.

Those skilled in the art recognize that ascorbic acid breaks down in the presence of oxygen (aerobic). A lesser known pathway is one in which no oxygen is present (anaerobic). Regardless of the pathway, the degradation occurs and carbon dioxide is generated. This challenges the conventional wisdom that ascorbic acid degradation can be slowed or stopped by removing oxygen or adding oxygen scavengers. The anaerobic pathway is evidence that ascorbic acid degradation will occur regardless of the presence of oxygen. Both pathways will yield carbon dioxide and eventually lead to excess gas generation and package failure without a method to address the carbon dioxide generation.

THE INVENTION

Figure 1:
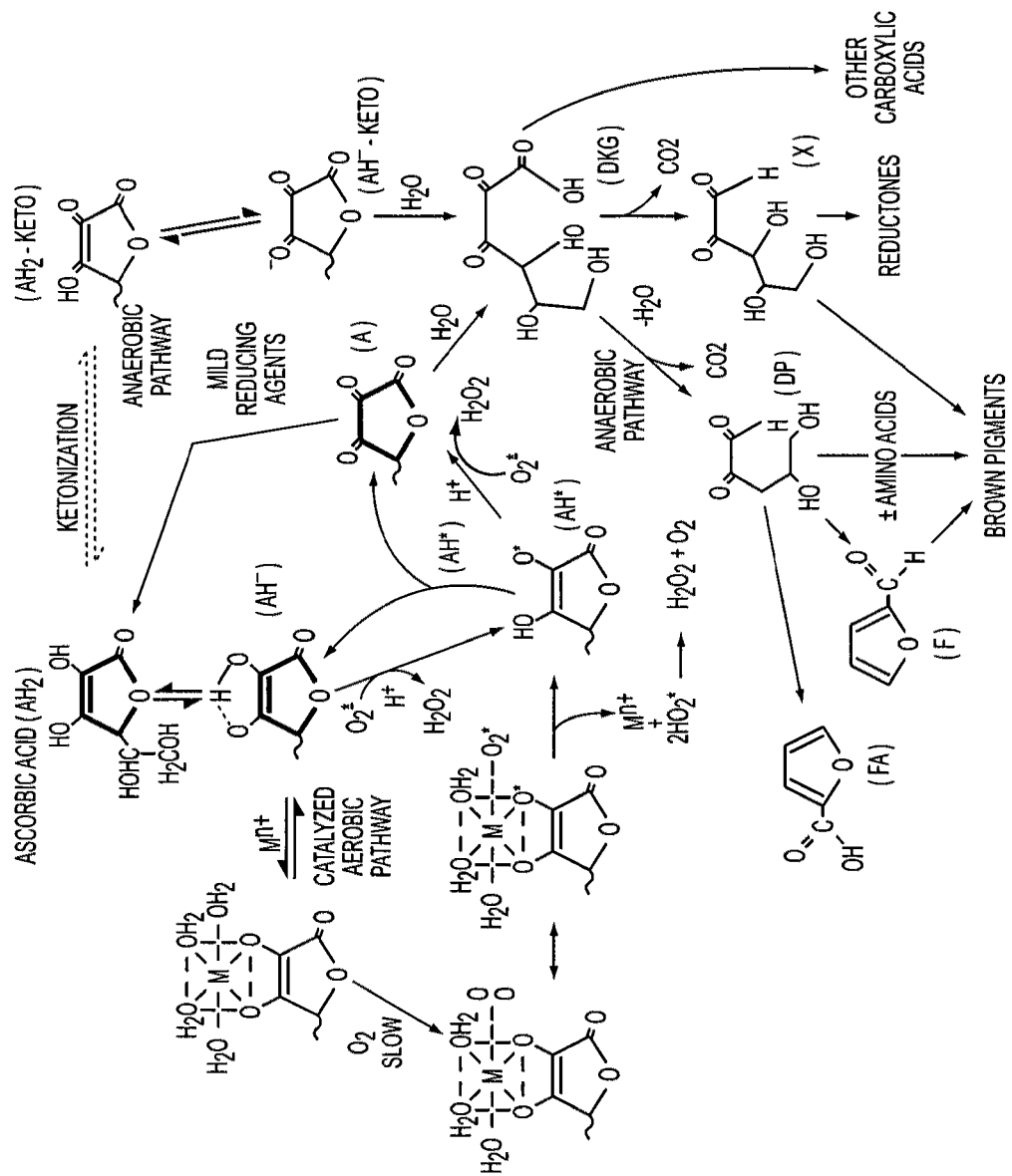
FIG. 1 shows the degradation pathway of ascorbic acid.
Figure 2:
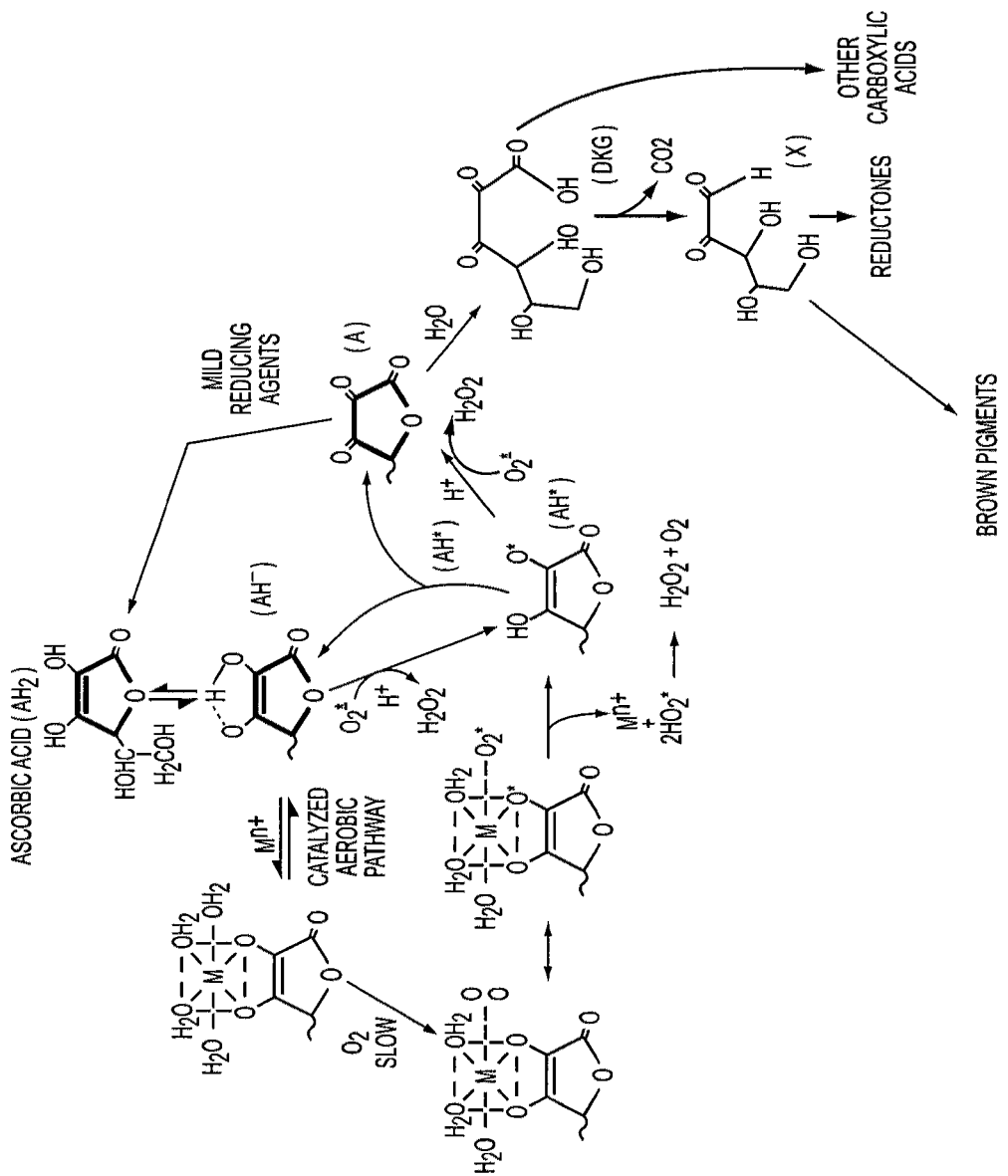
FIG. 2 shows the aerobic pathway of ascorbic acid degradation.
Figure 3:
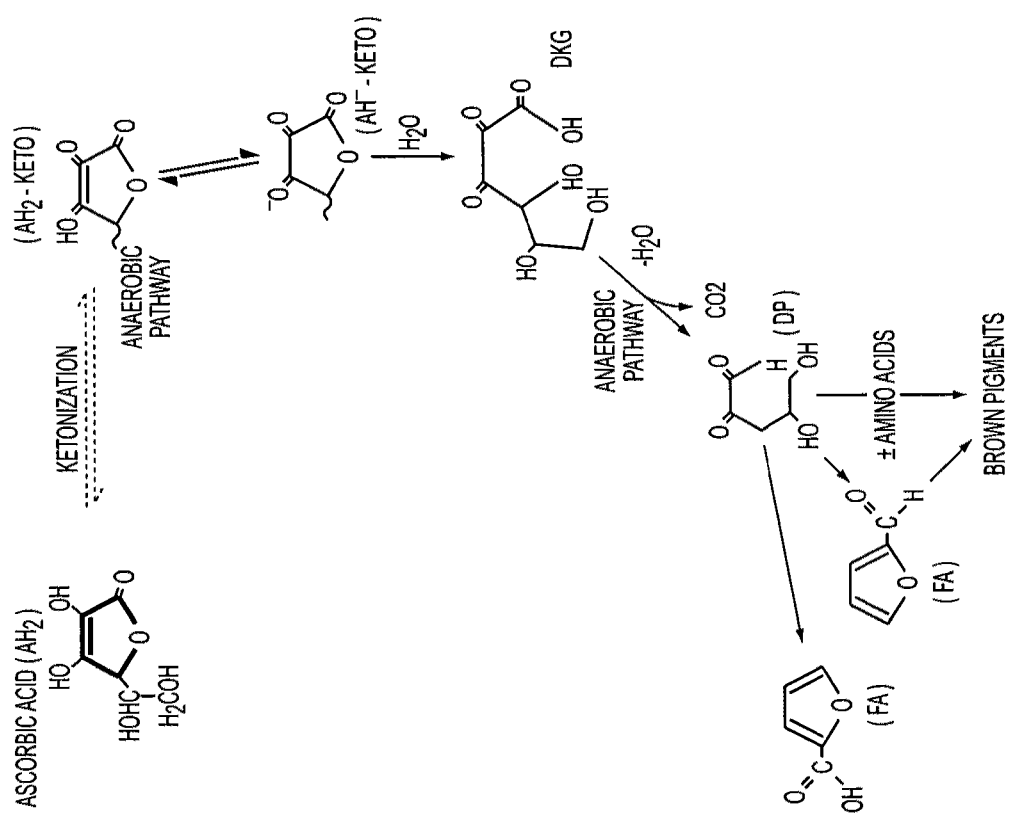
FIG. 3 shows the anaerobic pathway of ascorbic acid degradation.

FIG. 1 shows the degradation pathway of ascorbic acid. As reflected in FIG. 1, there are two degradation pathways. The aerobic pathway (FIG. 2) requires the presence of oxygen. If the oxygen is removed or consumed, the aerobic degradation reaction cannot proceed. When oxygen is not present, the degradation follows the anaerobic pathway (FIG. 3), which is independent of the presence of oxygen. Without being limited to mechanism, the degradation of ascorbic acid in semi-permeable packaging is roughly the same as the degradation in the prior art impermeable packaging. Regardless of the pathway, ascorbic acid will naturally decompose and yield carbon dioxide as a by-product.

Compositions containing ascorbic acid (about 0.1% to about 50% of the composition) are traditionally packaged in such a way that they are not exposed to oxygen or light. For compositions containing these levels of ascorbic acid, an amber bottle with a rubber dropper attached to a glass rod are typically used. When the package is sealed from gas transport, the carbon dioxide formed by degradation will build up and create undesirable effects.

The composition in this invention may be a lotion, gel, cream, serum, solution or liquid soap. Ascorbic acid is present at between about 0.1 to about 50%, preferably about 5 to about 20%, most preferably at about 15%. It is understood that ascorbic acid degrades over time and these percentages show ascorbic acid present when the composition is initially prepared.

The invention is an impermeable container with a semi-permeable top for containing compositions which comprise ascorbic acid. A preferred composition for this invention is a composition comprising ascorbic acid, more preferably at least about 0.1% by weight ascorbic acid in solution, and most preferably at least about 15% by weight ascorbic acid in solution. In one embodiment, this composition is located in a glass vial with a glass dropper, which has a silicone-bulb at the top.

The invention improves the shelf life of the packaging over the same composition in a glass vial with a glass dropper and a rubber bulb. It is believed that this invention will prevent unwanted pressurization in any type of impermeable container.

In this case, semi-permeable means a material which allows carbon dioxide permeation. Semi-permeable materials include, without limitation, silicone, kratan, isobutylene-isoprene, neoprene, and acrylonitrile-butadiene. This characteristic is important to the invention because of its ability to vent carbon dioxide generated, whether through aerobic or anaerobic pathways during the degradation of ascorbic acid. This phenomenon helps reduce excess pressure caused by carbon dioxide generation and prevents premature package failure.

Impermeable means a material which does not allow gasses and/or vapors to pass through the medium. Impermeable materials include, without limitation, glass, some rubbers (natural or synthetic), metal and some plastics.

Figure 4:
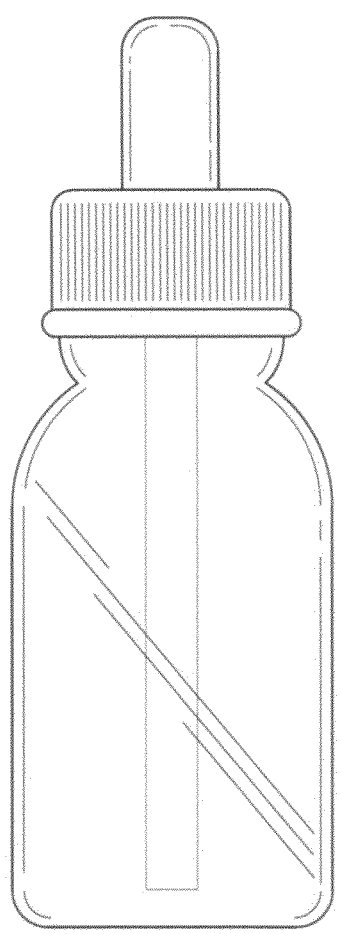
FIG. 4 is a sketch of a glass vial with a glass dropper and a silicone bulb.

In one embodiment of the invention, a composition containing ascorbic acid is packaged in an impermeable container which has a semi-permeable top, which is preferably, without limitation, a silicone bulb on a glass dropper. (See FIG. 4). The container may, without limitation, be glass, preferably amber glass. The silicone bulb may, without limitation, be attached to a glass dropper.

Semi-permeable material also permits water vapor to pass through it. This could result in a significant water weight loss for the composition. Additionally, it could also yield undesirable characteristics within the composition.

In compositions where significant water loss is a concern, certain considerations must be made. In the embodiment where a silicone bulb is used, the composition may come in physical contact with the large surface area of the bulb and allow water vapor to permeate, resulting in excess water loss. This could lead to undesirable results within the composition and premature product failure. When this is the case, a semi-permeable stopper, which has a much smaller surface area, could be placed on the end of the glass tube preventing the composition from coming in contact with the silicone bulb but still allowing for carbon dioxide transport. The scope of this invention includes all semi-permeable stoppers (e.g. without limitation caps, wedges, and plugs) that prevent the composition from travelling up the glass rod and into the bulb. By effectively preventing such an occurrence, the composition does not come into contact with the larger surface area of the bulb. In this specification, the headspace above the composition (which may contain some vapor from the composition) is not considered to be part of the composition. This prevents greater transport of other gasses such as water vapor across the semi-permeable membrane, and thus, limits larger magnitudes of overall weight loss that may result in package and/or product failure.

Figure 5:
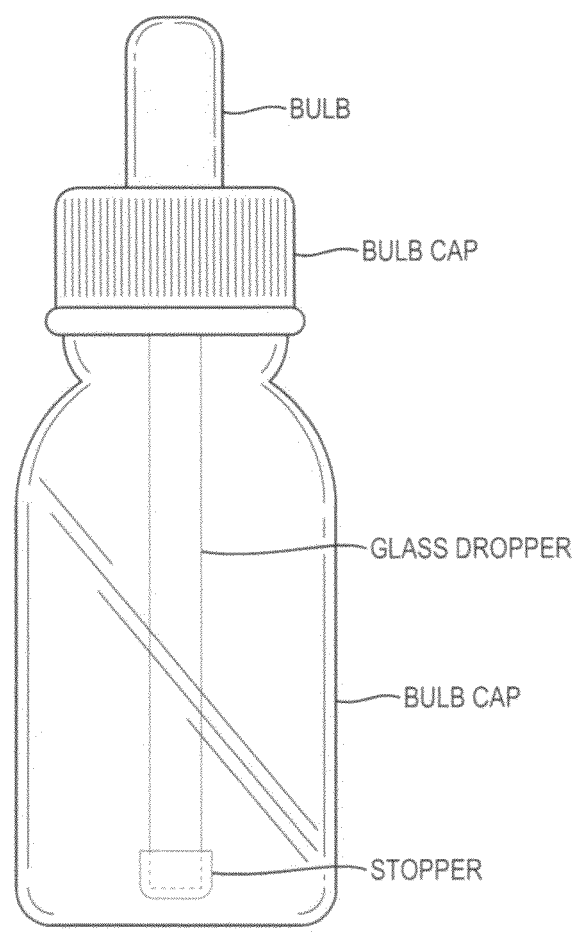
FIG. 5 is a sketch of a glass vial with a glass dropper and a silicone bulb, bulb cap and a silicone stopper.

In another embodiment, a composition containing ascorbic acid is packaged in a container which has a silicone bulb attached to a glass dropper. The container may, without limitation, be glass, preferably amber glass. Optionally, a silicone stopper is placed on the glass dropper at the end opposite the silicone bulb. FIG. 5 is a drawing of this embodiment. This silicone stopper is in place during shipment and storage, but is removed prior to use of the dropper.

Test 1

Figure 14:
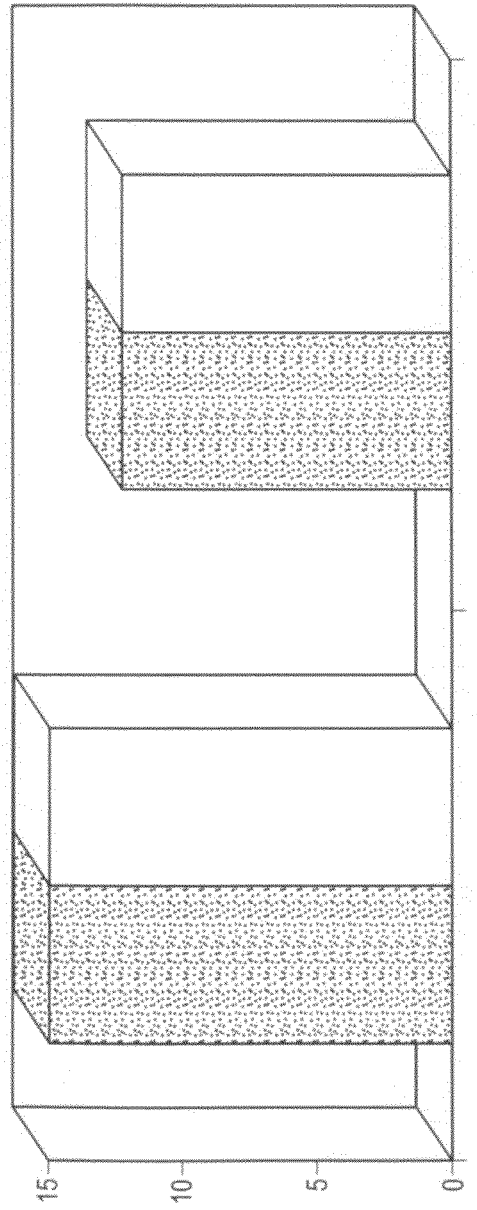
FIG. 14 is a chart showing the results of Test 1.

A composition, which was comprised of 15% ascorbic acid solution with a pH of 2.0-2.6, was placed in amber glass vials. One set was topped with a rubber bulb and glass dropper. The second set was topped with a silicone bulb and glass dropper. After 1 month at 50° C., the rubber bulb was at maximum expansion and the silicone bulb showed no signs of expansion or pressure. Additionally, they were tested for Vitamin C, which was initially present at 15%. The rubber dropper had 12.32% and the silicone dropper had 12.25%. The test confirmed that the rate of Vitamin C degradation is not significantly affected by the use of a semi-permeable membrane. FIG. 14 shows the results of this test.

Figure 11A:
FIGS. 11a and 11b are photos of Test 1's samples at Day 1 (50° C.).
Figure 11B:
Figure 12B:
FIGS. 12a and 12b are photos of Test 1's samples at Day 13 (50° C.).
Figure 12A:
Figure 13B:
FIGS. 13a and 13b are photos of Test 1's samples at Day 33 (50° C.).
Figure 13A:

FIGS. 11-13 show samples at different time intervals during this test. FIG. 11 is Day 1, FIG. 12 is Day 13, and FIG. 13 is Day 33, each at 50° C. As early as Day 13, it is evident that the use of silicone as the dropper bulb has eliminated the excessive gas leading to a package failure problem. Even at day 33, no signs of pressurization are evident in the package with the silicone bulb. No changes to the composition were required to achieve this result.

The invention allowed carbon dioxide to vent during ascorbic acid degradation, thus preventing excess pressure in the packaging. Even though the invention allowed semi-permeable material (silicone) to be used, there was no significant difference in the rate of ascorbic acid degradation between the impermeable (rubber bulb) and the semi-permeable (silicone) packaging (See FIG. 14).

Due to the unpredictable nature of shipping, one cannot be sure if the composition package will remain in an upright position during transit. Packages might be on their side or even inverted. That presents a challenge for this invention due to the nature of the silicone bulb and its permeability. Carbon dioxide gas will be prevalent within the headspace of the package because it is lighter than the composition. Water, on the other hand, will be prevalent within the composition because the composition contains water. Water vapor is defined as when a molecule of water transitions from a more associated (liquid) state to less associated (water vapor) state. While liquid water is in contact with the semi-permeable membrane, water vapor will transition out of the composition. If the package is turned on its side, water from the composition will be in contact with at least part of the bulb and will permeate through the silicone. When this is coupled with the expected permeation through the silicone bulb, excessive weight loss may occur. The next tests were conducted with some of the samples being placed on their side to monitor this phenomenon.

Test 2

A composition containing 15% ascorbic acid with a pH of 2.0-2.6 was prepared.

1. Eleven-1 oz amber glass vials were filled with 30 grams of composition and capped with rubber bulbs on glass droppers with black phenolic bulb caps.

2. One vial was placed in a 5° C. chamber.
3. One was placed in a 50° C. chamber.
4. One was kept at room temperature.
5. Five samples were placed in the 45° C. chamber upright.
6. Three samples were placed in the 45° C. chamber on their side.
7. Eleven-1 oz amber glass vials were filled with 30 grams of composition and capped with silicone bulbs on glass droppers with black phenolic bulb caps.
8. One vial was placed in a 5° C. chamber.
9. One was placed in a 50° C. chamber.
10. One was kept at room temperature.
11. Five samples were placed in the 45° C. chamber upright.
12. Three samples were placed in the 45° C. chamber on their side.

Samples were pulled at random intervals and tested for appearance and weight during the course of the 2-month study, with the exception of the 50° C. samples. All 50° C. tests were concluded at the end of the first month.

Figure 15:
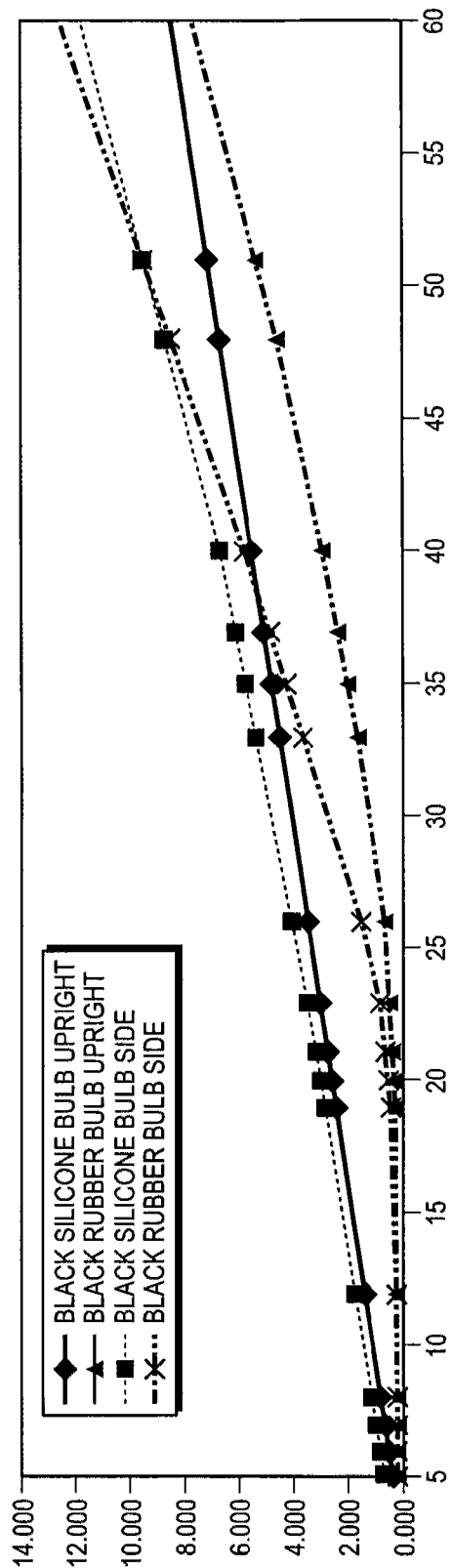
FIG. 15 is a graph showing the results of Test 2.

Table 1 summarizes the results of this test. The 50° C. results are not included in Table 1, because they were used for determining a 1-month accelerated trend, which was then further verified by the 2-month, 45° C. samples. (See also FIG. 15, which is a graphic representation of the results).

TABLE 1

| Rubber VS Silicone Bulb | |
| --- | --- |
| Day | Avg. Weight Loss |
| Black Rubber Bulb Upright at 45° C. | |
| 5 | 0.054 |
| 6 | 0.087 |
| 7 | 0.098 |
| 8 | 0.108 |
| 12 | 0.195 |
| 19 | 0.390 |
| 20 | 0.423 |
| 21 | 0.445 |
| 23 | 0.520 |
| 26 | 0.683 |
| 33 | 1.627 |
| 35 | 1.984 |
| 37 | 2.342 |
| 40 | 2.906 |
| 48 | 4.674 |
| 51 | 5.433 |
| 68 | 9.922 |
| Black Rubber Bulb Side at 45° C. | |
| 5 | 0.054 |
| 6 | 0.097 |
| 7 | 0.108 |
| 8 | 0.108 |
| 12 | 0.227 |
| 19 | 0.509 |
| 20 | 0.617 |
| 21 | 0.714 |
| 23 | 0.936 |
| 26 | 1.591 |
| 33 | 3.680 |
| 35 | 4.264 |
| 37 | 4.827 |
| 40 | 5.801 |
| 48 | 8.604 |
| 51 | 9.643 |
| 68 | 15.303 |
| Black Silicone Bulb Upright at 45° C. | |
| 5 | 0.455 |
| 6 | 0.595 |
| 7 | 0.725 |
| 8 | 0.834 |
| 12 | 1.418 |

TABLE 1-continued

| Rubber VS Silicone Bulb | |
| --- | --- |
| Day | Avg. Weight Loss |
| 19 | 2.371 |
| 20 | 2.533 |
| 21 | 2.642 |
| 23 | 2.934 |
| 26 | 3.389 |
| 33 | 4.428 |
| 35 | 4.720 |
| 37 | 5.045 |
| 40 | 5.500 |
| 48 | 6.658 |
| 51 | 7.102 |
| 68 | 9.689 |
| Black Silicone Bulb Side at 45° C. | |
| 5 | 0.617 |
| 6 | 0.736 |
| 7 | 0.919 |
| 8 | 1.038 |
| 12 | 1.698 |
| 19 | 2.802 |
| 20 | 3.007 |
| 21 | 3.137 |
| 23 | 3.451 |
| 26 | 4.035 |
| 33 | 5.343 |
| 35 | 5.744 |
| 37 | 6.122 |
| 40 | 6.706 |
| 48 | 8.697 |
| 51 | 9.643 |
| 68 | 13.867 |

Although silicone appears to lose more weight initially compared to rubber, it eventually outperforms the rubber. This is believed (without limitation) to be due to the impermeable nature of the rubber medium. Because the rubber is not permeable to the carbon dioxide production, it expands and eventually becomes porous allowing water vapor to escape. The silicone, on the other hand, does not expand and the water vapor transport remains constant and linear over time.

As mentioned earlier, silicone is permeable to both carbon dioxide and water vapor. There is more water vapor in the composition than there is in the headspace and therefore more transport will occur when the composition is in actual contact with the silicone membrane. The silicone bulb has a large surface area and as pressure builds within the package, the composition travels up the glass tube and into the silicone bulb thereby becoming exposed to a large surface area that is permeable to water vapor. A small silicone cap that fits on the end of the glass tube will prevent the composition for coming in contact with the silicone bulb while still allowing the transport of carbon dioxide up the tube and eventually through the silicone bulb. By preventing the composition from traveling up the glass tube but still allowing the transport of carbon dioxide gas, we effectively limit the amount of water vapor transport and reduce the unwanted weight loss.

Test 3

A composition containing 15% ascorbic acid with a pH of 2.0-2.6 was prepared.

1. Eleven-1 oz amber glass vials were filled with 30 grams of composition and capped with silicone bulbs on glass droppers with black phenolic bulb caps. A small silicone stopper was placed on the end of the glass rod. (See FIG. 5)
2. One vial was placed in a 5° C.
3. One was placed in a 50° C. chamber.
4. One was kept at room temperature.

5. Four samples were placed in the 45° C. chamber upright.
6. Four samples were placed in the 45° C. chamber on their side.

Samples were pulled at random intervals and tested for appearance and weight during the course of the 2-month study, with the exception of the 50° C. samples. All 50° C. tests were concluded at the end of the first month.

Figure 6:
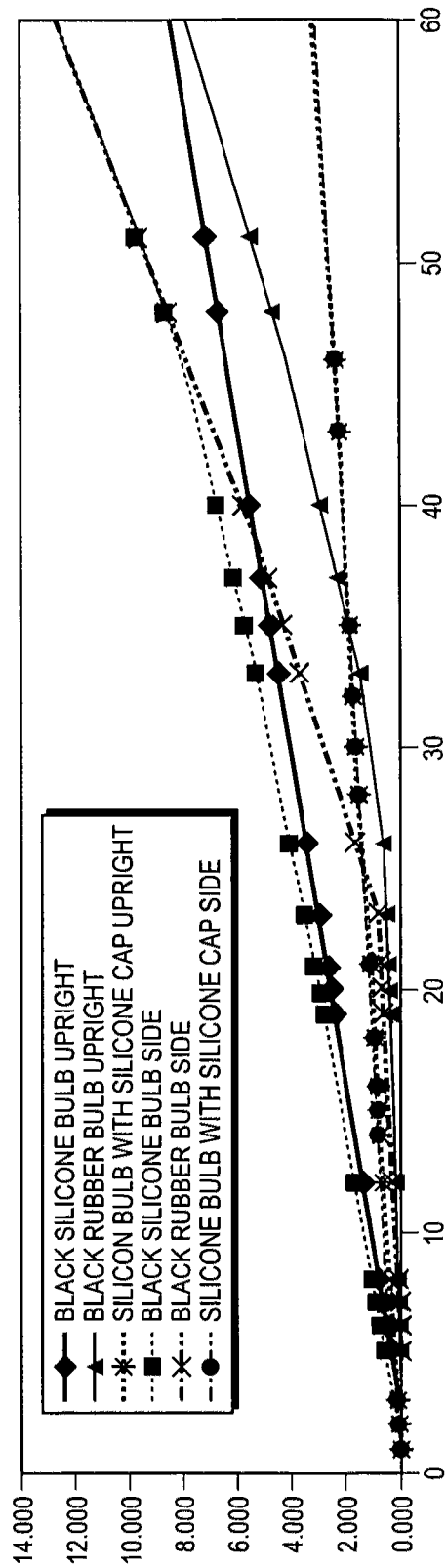
FIG. 6 is a graph showing the results of Test 3.

Table 2 summarizes the results of this test. The 50° C. results are not included in Table 2, because they were used for determining a 1-month accelerated trend, which was then further verified by the 2-month, 45° C. samples. See also FIG. 6 for the graphic results.

TABLE 2

| Silicone Bulb with Silicone Cap | |
|---|---|
| Day | Avg. Weight Loss |
| Silicone Bulb with Silicone Cap Upright | |
| 1 | 0.076 |
| 2 | 0.119 |
| 3 | 0.206 |
| 7 | 0.488 |
| 14 | 0.846 |
| 15 | 0.889 |
| 16 | 0.933 |
| 18 | 1.052 |
| 21 | 1.193 |
| 28 | 1.561 |
| 30 | 1.702 |
| 32 | 1.822 |
| 35 | 1.952 |
| 43 | 2.375 |
| 46 | 2.527 |
| 63 | 3.492 |
| Silicone Bulb with Silicone Cap Side | |
| 1 | 0.087 |
| 2 | 0.130 |
| 3 | 0.206 |
| 7 | 0.455 |
| 14 | 0.801 |
| 15 | 0.823 |
| 16 | 0.877 |
| 18 | 0.963 |
| 21 | 1.093 |
| 28 | 1.493 |
| 30 | 1.569 |
| 32 | 1.656 |
| 35 | 1.807 |
| 43 | 2.240 |
| 46 | 2.370 |
| 63 | 3.247 |

The data shows that the silicone cap has prevented unwanted water loss due to vapor permeation occurring in the silicone bulb. Upon opening the samples at the completion of the test, no appreciable gas build-up was observed. This was confirmation that excess carbon dioxide build-up was prevented even with this configuration.

Other packaging options were investigated to see if another style of cap would produce similar results. Commercially available silicone products such as a silicone wedge and a silicone plug were evaluated. Both the silicone wedge and plug were the appropriate diameter to fit in the hole in the glass tube.

Test 4

A composition containing 15% ascorbic acid with a pH of 2.0-2.6 was prepared.

Figure 7:
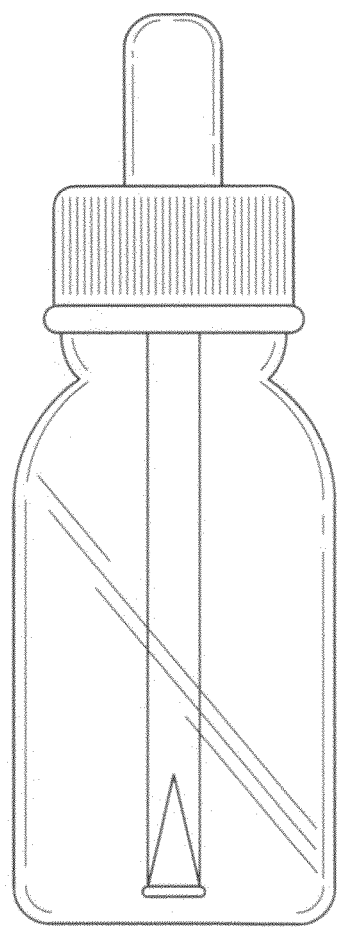
FIG. 7 is a sketch of a glass vial with a glass dropper and a silicone bulb and a silicone wedge.
Figure 8:
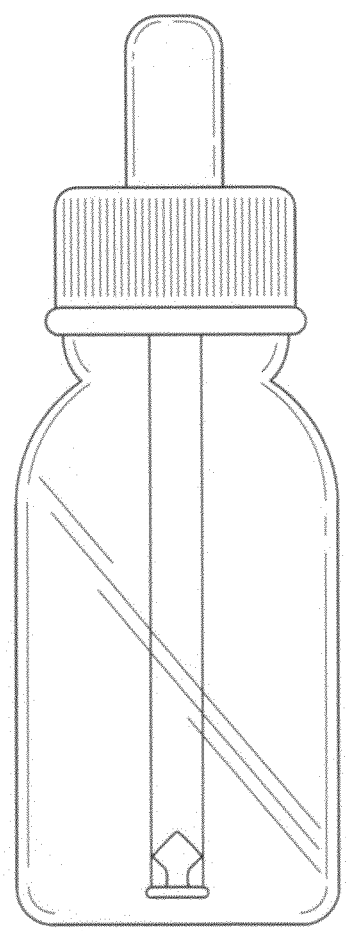
FIG. 8 is a sketch of a glass vial with a glass dropper and a silicone bulb and a silicone plug.

1. Eleven-1 oz amber glass vials were filled with 30 grams of composition and capped with silicone bulbs on glass droppers with black phenolic bulb caps. A small silicone wedge was placed inside the end of the glass rod. (See FIG. 7)
2. One vial was placed in a 5° C.
3. One was placed in a 50° C. chamber.
4. One was kept at room temperature.
5. Five samples were placed in the 45° C. chamber upright.
6. Three samples were placed in the 45° C. chamber on their side.
7. Eight-1 oz amber glass vials were filled with 30 grams of composition and capped with silicone bulbs on glass droppers with black phenolic bulb caps. A small silicone plug was placed inside the end of the glass rod. (See FIG. 8)
8. Four samples were placed in the 45° C. chamber upright.
9. Four samples were placed in the 45° C. chamber on their side.

Samples were pulled at random intervals and tested for appearance and weight during the course of the 2-month study, with the exception of the 50° C. samples. All 50° C. tests were concluded at the end of the first month.

Figure 9:
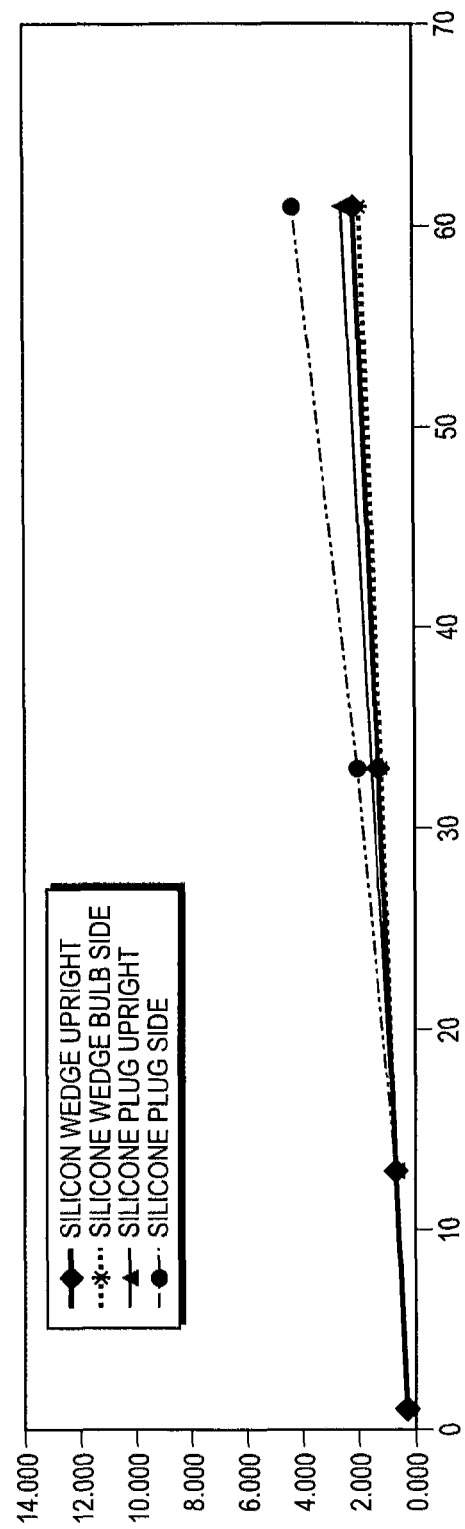
FIG. 9 is a graph showing the results of Test 4.

Table 3 summarizes the results of this test. The 50° C. results are not included in Table 3, because they were used for determining a 1-month accelerated trend, which was then further verified by the 2-month, 45° C. samples. See also FIG. 9 for the graphic results.

TABLE 3

| Silicone Wedge and Silicone Plug | |
|---|---|
| Day | Avg. Weight Loss |
| Silicone Wedge Upright | |
| 1 | 0.033 |
| 14 | 0.460 |
| 34 | 1.673 |
| 63 | 1.827 |
| Silicone Wedge Side | |
| 1 | 0.033 |
| 14 | 0.456 |
| 34 | 2.092 |
| 63 | 1.990 |
| Silicone Plug Upright | |
| 1 | 0.041 |
| 14 | 0.571 |
| 34 | 1.405 |
| 63 | 2.501 |
| Silicone Plug Side | |
| 1 | 0.035 |
| 14 | 0.486 |
| 34 | 1.894 |
| 63 | 4.203 |

Upon completion of the test, all samples were evaluated for excess carbon dioxide build-up. None of the samples showed overpressurization. The test results prove that inserting a semi-permeable material into the end of the glass rod effectively reduced the excess weight loss while still allowing generated carbon dioxide to vent the package.

A control test was performed to determine what adverse effects there are from placing an air-tight service cap on the package in place of the rubber bulb.

Test 5

A composition containing 15% ascorbic acid with a pH of 2.0-2.6 was prepared.

1. Thirteen-1 oz amber glass vials were filled with 30 grams of composition and capped with a black phenolic service cap with a poly-cone liner.
2. One vial was placed in a 5° C. chamber.
3. One was placed in a 50° C. chamber.
4. One was kept at room temperature.

5. Ten samples were placed in the 45° C. chamber upright.

Five samples were pulled at one month and five samples were pulled at two months to test for pressure build-up within the package.

At one month, all samples exhibited signs of gas production and over-pressurization by foaming slightly upon opening. The two month samples exhibited over-pressurization and foamed out of the bottle upon opening.

This test confirms the overpressurization of the package that can take place when Vitamin C breaks down anaerobically in a hermetically sealed container. It also confirms the validity of using a semi-permeable membrane to vent unwanted carbon dioxide that results from the breakdown of ascorbic acid.

Figure 10:
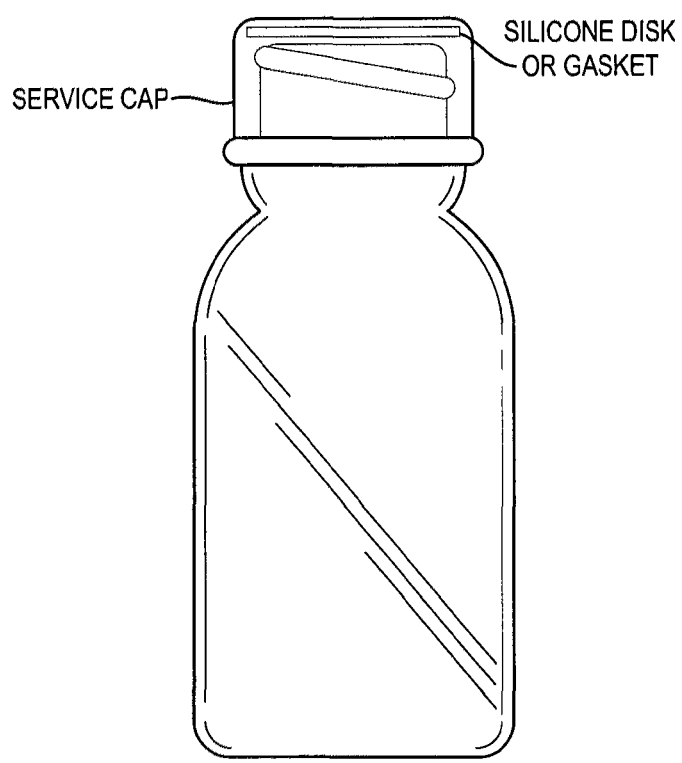
FIG. 10 is a sketch of a glass vial with a glass dropper and a service cap with a silicone gasket or disc.

A washer or a silicone disc, similar to a washer but without a hole in the middle, can be placed between the service cap and the glass vial to act as the semi-permeable membrane to vent any unwanted build-up of carbon dioxide (the "gasket"). Because of the nature of the silicone gasket, we can take advantage of its inherent properties of venting carbon dioxide without the need of a silicone bulb or some silicone barrier between the bulb and the glass rod. The venting would be slower due to the considerably lowered surface area but could be sufficient to continue venting after the composition has been transported to its final destination and is in a controlled temperature environment. In this scenario, any excess carbon dioxide that had built up would continue to vent through the gasket while the production of carbon dioxide will slow with the lowered temperature storage. (See FIG. 10).

Test 6

A test was performed to evaluate the benefit of using a silicone washer placed inside a phenolic service cap whose polycone liner had been removed. Control samples were prepared for comparison, using the phenolic cap with polycone liner still intact. The goal of this test was to determine whether the silicone washer would continue to allow the slow release of any overproduction of carbon dioxide, eventually leading to a non-pressurized composition, yet limiting the amount of weight loss associated with water vapor transport. After a 1-month incubation period at 50° C., each sample was shaken for 10 seconds prior to opening (to simulate a worst case scenario). Only one sample was opened per day.

A composition containing 15% ascorbic acid with a pH of 2.0-2.6 was prepared.
1. Six-1 oz amber glass vials were filled with 30 grams of composition and capped with a black phenolic cap with a poly-cone liner.
2. Six-1 oz amber glass vials were filled with 30 grams of composition and capped with a black phenolic cap with the poly-cone liner removed and subsequently fitted with a silicone washer.
3. All 12 samples were placed in a 50° C. chamber for 30 days.

At the conclusion of the 30 day incubation period, all samples were brought to room temperature for the remainder of the study. Immediately, one sample of each set was opened after being shaken for 10 seconds to release any dissolved gas. This continued over the course of an 8-day period, with one sample of each set being opened per day. Observations regarding the appearance of gas, the sound of gas escaping and the amount of product overflowing out of the vial were recorded.

The samples with the poly-cone liner service cap, as expected, had considerable amounts of dissolved gas and overflowed violently upon opening leading to excessive weight loss. This phenomenon continued until the test was concluded. The samples with the silicone washer showed initial signs of overpressurization with the sound of gas escaping upon opening. However, this diminished each day as the test continued, finally ending in only a faint sound of gas escaping. Moreover, at no time did the samples with the silicone washer show any indications that a "champagne" effect or overflow could happen.

Table 4 summarizes the results of this test.

TABLE 4

Champagne Effect Test - 30 Days at 50° C.

| Sample # | Description | Day | Observations | Product Loss After Opening |
|---|---|---|---|---|
| 15 | Phenolic Cap w/Poly-cone Liner | 1 | Champagne effect - overflowing | 25.31% |
| 35 | Phenolic Cap with Silicone Washer | 1 | Slight gassing with bubbles. No overflow | 0.00% |
| 16 | Phenolic Cap w/Poly-cone Liner | 2 | Champagne effect - overflowing | 10.49% |
| 36 | Phenolic Cap with Silicone Washer | 2 | Slight gassing with bubbles. No overflow | 0.00% |
| 17 | Phenolic Cap w/Poly-cone Liner | 3 | Champagne effect - overflowing | 54.13% |
| 37 | Phenolic Cap with Silicone Washer | 3 | Slight gassing with bubbles. No overflow | 0.00% |
| 18 | Phenolic Cap w/Poly-cone Liner | 6 | Champagne effect - overflowing | 53.03% |
| 38 | Phenolic Cap with Silicone Washer | 6 | Slight gassing with no overflow. No bubbles | 0.00% |
| 19 | Phenolic Cap w/Poly-cone Liner | 7 | Champagne effect - overflowing | 51.95% |
| 39 | Phenolic Cap with Silicone Washer | 7 | Slight gassing with no overflow. No bubbles | 0.00% |
| 20 | Phenolic Cap w/Poly-cone Liner | 8 | Champagne effect - overflowing | 65.24% |
| 40 | Phenolic Cap with Silicone Washer | 8 | Very slight gassing with no overflow. No bubbles | 0.00% |

The data confirms that by utilizing the inherent properties of a semi-permeable membrane, we can successfully vent the unwanted overproduction of gas without venting water vapor to a degree that would be deleterious to the composition. This can be done with a plug or cap attached to the glass rod to lower surface area contact with the composition, or through a service cap with a semi-permeable liner (e.g. without limitation a gasket, washer or silicone disc).

In another embodiment, the composition is located in an impermeable container with a top. The top is a service cap with a semi-permeable liner, and the container is intended for use as a syringe bottle. The user would pierce the service cap and semi-permeable liner with the syringe needle to access the composition.

It is to be understood that while the invention has been described in conjunction with the detailed description thereof, that the foregoing description is intended to illustrate and not limit the scope of the invention, which is defined by the scope of the appended claims. Other aspects, advantages, and modifications are evident from a review of the following claims.

What is claimed is:

1. A method of venting by-products of degradation of a composition containing ascorbic acid and reducing water vapor loss comprising packaging the composition in an impermeable container, a glass dropper, and a top, wherein the top comprises a first semi-permeable material, wherein the semi-permeable material is present as a bulb attached to a first end of the glass dropper, and a stopper is attached to a second end of the glass dropper, wherein the stopper comprises a second semi-permeable material, and wherein the composition comprises water.

2. The method of claim 1 wherein the impermeable container comprises glass.

3. The method of claim 1 wherein the first semi-permeable material comprises silicone.

4. The method of claim 1 wherein the composition is one or more selected from the group consisting of liquid, gel, lotion, cream and serum.

5. The method of claim 1 further comprising improving package integrity life.

6. The method of claim 1 wherein the composition comprises between about 0.1 and about 50% ascorbic acid.

7. The method of claim 1 wherein the composition comprises about 15% ascorbic acid.

8. The method of claim 1 wherein the composition comprises between about 5% and about 20% ascorbic acid.

9. The method of claim 1 wherein the first semi-permeable material and the second semi-permeable material are same materials.

10. The method of claim 1 wherein the first semi-permeable material and the second semi-permeable material are different materials.

11. The method of claim 1 wherein the stopper is one or more of the group consisting of a cap, a wedge, and a plug.

12. The method of claim 1 wherein a surface of the second semi-permeable material contacting the composition is less than a surface area of the first semi-permeable material.

13. The method of claim 1 wherein the composition is a pharmaceutical composition.

14. The method of claim 1 wherein the composition is a cosmetic composition.

15. The method of claim 1 wherein the composition comprises one or more of the group consisting of a solution and a liquid soap.

16. The method of claim 1 wherein the composition is edible by animals.

17. The method of claim 1 wherein the top further comprises an impermeable cap and wherein the semi-permeable material is a liner located between the impermeable cap and the impermeable container.

18. The method of claim 17 wherein the liner is selected from the group consisting of a gasket, liner and disc.

* * * * *